US012746074B2

(12) United States Patent
Lacal et al.

(10) Patent No.: US 12,746,074 B2
(45) Date of Patent: Sep. 29, 2026

(54) SYSTEMS AND METHODS FOR PROVIDING GUIDANCE FOR A ROBOTIC MEDICAL PROCEDURE

(71) Applicant: MAKO Surgical Corporation, Weston, FL (US)

(72) Inventors: Jose C. Lacal, Boynton Beach, FL (US); David B. Berman, Miami, FL (US); Abdullah Z. Abbasi, Plantation, FL (US)

(73) Assignee: MAKO Surgical Corporation, Fort Lauderdale, FL (US)

( * ) Notice: Subject to any disclaimer, the term of this patent is extended or adjusted under 35 U.S.C. 154(b) by 86 days.

(21) Appl. No.: 18/768,423

(22) Filed: Jul. 10, 2024

(65) Prior Publication Data

US 2024/0366316 A1 Nov. 7, 2024

Related U.S. Application Data

(63) Continuation of application No. 17/559,000, filed on Dec. 22, 2021, now Pat. No. 12,059,217, which is a (Continued)

(51) Int. Cl.

*A61B 34/00* (2016.01)
*A61B 34/10* (2016.01)

(Continued)

(52) U.S. Cl.

CPC .............. *A61B 34/25* (2016.02); *A61B 34/10* (2016.02); *A61B 34/20* (2016.02); *A61B 34/30* (2016.02);

(Continued)

(58) Field of Classification Search

CPC ......... A61B 34/25; A61B 34/10; A61B 34/20; A61B 34/30; A61B 34/35;

(Continued)

(56) References Cited

U.S. PATENT DOCUMENTS

2003/0109780 A1 6/2003 Coste-Maniere et al.
2004/0030245 A1 2/2004 Noble et al.

(Continued)

FOREIGN PATENT DOCUMENTS

KR 10-2012-0013955 A 2/2012
WO WO 2008039243 A1 4/2008

OTHER PUBLICATIONS

Sep. 12, 2016—(PCT) International Search Report and Written Opinion, App. No. PCT/US2016/032331.

(Continued)

*Primary Examiner* — Ryan Rink

(74) *Attorney, Agent, or Firm* — Bookoff McAndrews, PLLC

(57) ABSTRACT

A computer-implemented method for generating and presenting an electronic display of guidance for performing a robotic medical procedure may include receiving a plurality of prior procedure data sets; receiving or identifying objective data defining one or more of a duration or a patient outcome of the robotic medical procedure; executing an algorithm to identify a pattern across the plurality of prior procedure data sets; receiving information about an instance of the robotic medical procedure to be performed in the future for a patient outside the population; automatically generating guidance for performing the robotic medical procedure; and generating and presenting an electronic display of the guidance for performing the robotic medical procedure.

19 Claims, 4 Drawing Sheets

Related U.S. Application Data continuation of application No. 16/254,854, filed on Jan. 23, 2019, now Pat. No. 11,234,774, which is a continuation of application No. 15/154,122, filed on May 13, 2016, now Pat. No. 10,226,302.

(60) Provisional application No. 62/162,430, filed on May 15, 2015.

(51) Int. Cl.

| | |
|---|---|
| ***A61B 34/20*** | (2016.01) |
| ***A61B 34/30*** | (2016.01) |
| ***A61B 34/35*** | (2016.01) |
| ***B25J 9/16*** | (2006.01) |
| ***G09B 5/02*** | (2006.01) |
| ***G16H 20/40*** | (2018.01) |
| ***G16H 40/63*** | (2018.01) |
| ***G16H 50/20*** | (2018.01) |
| ***G16H 50/70*** | (2018.01) |

(52) U.S. Cl.

CPC ............. *A61B 34/35* (2016.02); *B25J 9/1664* (2013.01); *B25J 9/1689* (2013.01); *G09B 5/02* (2013.01); *G16H 20/40* (2018.01); *G16H 40/63* (2018.01); *G16H 50/20* (2018.01); *G16H 50/70* (2018.01); *A61B 2034/107* (2016.02); *A61B 2034/108* (2016.02); *A61B 2034/2055* (2016.02); *A61B 2034/252* (2016.02); *A61B 2034/254* (2016.02); *A61B 2034/256* (2016.02); *A61B 2034/258* (2016.02)

(58) Field of Classification Search

CPC ........ A61B 2034/107; A61B 2034/108; A61B 2034/2055; A61B 2034/252; A61B 2034/254; A61B 2034/256; A61B 2034/258; B25J 9/1664; B25J 9/1689; G09B 5/02; G16H 20/40; G16H 40/63; G16H 50/20; G16H 50/70

See application file for complete search history.

(56) References Cited

U.S. PATENT DOCUMENTS

| | | | |
|---|---|---|---|
| 2004/0034302 | A1* | 2/2004 | Abovitz ................. B25J 13/025 600/428 |
| 2004/0068187 | A1 | 4/2004 | Krause et al. |
| 2008/0077158 | A1 | 3/2008 | Haider et al. |
| 2010/0249533 | A1 | 9/2010 | Pierce et al. |
| 2010/0249534 | A1 | 9/2010 | Pierce et al. |
| 2010/0249535 | A1 | 9/2010 | Pierce et al. |
| 2010/0250276 | A1 | 9/2010 | Pierce et al. |
| 2010/0250284 | A1 | 9/2010 | Pierce et al. |
| 2010/0250571 | A1 | 9/2010 | Pierce et al. |
| 2014/0081659 | A1 | 3/2014 | Nawana et al. |
| 2014/0148816 | A1 | 5/2014 | McDonald et al. |
| 2015/0057675 | A1 | 2/2015 | Akeel et al. |
| 2016/0015473 | A1 | 1/2016 | Frimer et al. |
| 2016/0034664 | A1 | 2/2016 | Santos et al. |
| 2016/0283676 | A1 | 9/2016 | Lyon et al. |
| 2016/0324580 | A1 | 11/2016 | Esterberg |
| 2017/0049517 | A1 | 2/2017 | Felder et al. |
| 2017/0212723 | A1 | 7/2017 | Atarot et al. |
| 2017/0239000 | A1 | 8/2017 | Moctezuma et al. |

OTHER PUBLICATIONS

Korean Grant of Patent in corresponding Korean Application No. 10-2021-7035725, dated Dec. 13, 2021 (2 pages).

* cited by examiner

SYSTEMS AND METHODS FOR PROVIDING GUIDANCE FOR A ROBOTIC MEDICAL PROCEDURE

CROSS REFERENCE TO RELATED APPLICATION

This application is a continuation of U.S. application Ser. No. 17/559,000, filed Dec. 22, 2021, which is a continuation of U.S. application Ser. No. 16/254,854, filed Jan. 23, 2019, Now U.S. Pat. No. 11,234,774, which is a continuation of U.S. application Ser. No. 15/154,122, now U.S. Pat. No. 10,226,302, which claims priority to U.S. Provisional Application No. 62/162,430, filed May 15, 2015, the entirety entireties of which are incorporated by reference herein.

TECHNICAL FIELD

Embodiments of the present disclosure relate generally to providing guidance for robotic surgical procedures. More specifically, the present disclosure relates to collecting and analyzing data from prior procedures to develop guidance for a robotic surgical procedure.

BACKGROUND

Medical practitioners may use robotic devices to aid in carrying out medical procedures. Robotic devices may work in connection with a computer system and other devices (e.g., components of a navigation system) to form a robotic system. The robotic system may receive and store various information related to a specific procedure to be carried out by the practitioner, such as information about a patient and a surgical plan. For a knee surgery, for example, the surgical plan might include the type of procedure to be performed (e.g., total knee replacement or unicondylar procedure), the tissue and bone modifications necessary to prepare the bone to receive an implant, and the type of implant to be implanted within the patient. The robotic system may also perform various functions during implementation of the surgical plan, such as tracking the patient and helping the practitioner modify the patient's anatomy (e.g., tissue, bone) according to the plan.

Robotic systems may also acquire information during medical procedures. This information may relate to any number of characteristics of the medical procedure. The information may describe specific characteristics of the implementation of a procedure, such has how long a certain portion of a procedure took, which tools were used during the procedure, or how a practitioner accomplished certain bone modifications. The information may also describe characteristics of the procedure related to the patient, the environment, or other inputs related to the procedure. For example, the characteristics may be the patient's height, weight, type of procedure that was performed, or operating room setup.

SUMMARY

Embodiments of the present disclosure relate to, among other things, retrieving and analyzing information acquired during robotic medical procedures to provide guidance for robotic medical procedures. Each of the embodiments disclosed herein may include one or more of the features described in connection with any of the other disclosed embodiments.

In one example, a computer-implemented method for generating and presenting an electronic display of guidance for performing a robotic medical procedure may include receiving, by one or more processors, a plurality of prior procedure data sets, wherein each prior procedure data set: i) corresponds to an instance of the robotic medical procedure performed by using a robotic tool on a patient within a population, and ii) defines one or more of a location or a movement of the patient, a medical device, or the robotic tool involved in the robotic medical procedure; a force applied by the robotic tool; or a timing of a step of the robotic medical procedure; receiving or identifying, by the one or more processors, objective data defining one or more of a duration or a patient outcome of the robotic medical procedure; executing an algorithm, stored in a non-transitory computer-readable storage medium, to identify a pattern across the plurality of prior procedure data sets, the pattern describing one or more of a location or a movement of a patient, medical device, or robotic tool involved in the robotic medical procedure, a force applied by the robotic tool, or a timing of a step of the robotic medical procedure that achieves the duration or the patient outcome defined by the objective data; receiving, by the one or more processors, information about an instance of the robotic medical procedure to be performed in the future for a patient outside the population; automatically generating, by the one or more processors, guidance for performing the robotic medical procedure, the guidance comprising a recommended location or movement of a patient, medical device, or robotic tool involved in the robotic medical procedure, force applied by the robotic tool, or timing of a step of the robotic medical procedure based on evaluating the pattern identified across the plurality of prior procedure data sets and the information received about the instance of the robotic medical procedure to be performed; and generating and presenting an electronic display of the guidance for performing the robotic medical procedure.

The method may additionally or alternatively include one or more of the following features or steps: the duration defined by the objective data may be a duration of a portion of the robotic medical procedure; identifying the pattern across the plurality of prior procedure data sets may include identifying an occurrence level of at least one of the location or the movement of the patient, medical device, or robotic tool across the plurality of prior procedure data sets; identifying the pattern across the plurality of prior procedure data sets may include describing a movement of the robotic tool during a portion of a procedure that achieves the duration defined by the objective data, wherein the duration is of the portion of the robotic medical procedure; the information about the instance of the robotic medical procedure to be performed may include information about at least one of: a patient, a type of procedure, an operating room characteristic, or a user's prior experience; the guidance may comprise a recommended timing of a step of the robotic medical procedure, and the recommendation may include a recommended order of steps of the robotic medical procedure.

In another example, a system for generating and presenting an electronic display of guidance for performing a robotic medical procedure may include a computer-readable storage medium storing instructions for generating and presenting an electronic display of guidance for performing the robotic medical procedure; and one or more processors configured to execute the instructions to perform a method including: receiving a plurality of prior procedure data sets, wherein each prior procedure data set: i) corresponds to an instance of the robotic medical procedure performed using a robotic tool on a patient within a population, and ii) includes robot data obtained from a robotic device associated with the robotic tool; receiving or identifying objective data defining or more of a duration or a patient outcome of the robotic medical procedure; identifying a pattern across the plurality of prior procedure data sets, the pattern describing a characteristic of the robotic medical procedure that achieves the duration or the patient outcome defined by the objective data; receiving information about an instance of the robotic medical procedure to be performed in the future for a patient outside the population; automatically generating guidance for performing the robotic medical procedure based on the characteristic identified by the pattern and the information received about the instance of the robotic medical procedure to be performed; and generating and presenting an electronic display of the guidance for performing the robotic medical procedure.

The system may additionally or alternatively include one or more of the following features or steps: the characteristic of the robot data may be one or more of a location or a movement of a patient, medical device, or robotic tool involved in the robotic medical procedure, a force applied by the robotic tool, or a timing of a step of the robotic medical procedure; the guidance may comprise a recommended location or movement of a patient, medical device, or robotic tool involved in the robotic medical procedure, force applied by the robotic tool, or timing of a step of the robotic medical procedure; the robot data may include information gathered by the robotic device during the corresponding instance of the robotic medical procedure; identifying the pattern may include determining an occurrence level of the characteristic across the plurality of input procedures; the characteristic may be an order of procedure steps, and identifying the pattern may include determining the order of procedure steps that achieves the duration defined by the objective data; and the information about the instance of the robotic medical procedure to be performed may include information about at least one of: a patient, a type of procedure, an operating room characteristic, or a user's prior experience.

In yet another example, a non-transitory computer-readable storage medium may have instructions thereon that, when executed by a processor, cause the processor to perform a method for generating and presenting an electronic display of guidance for performing a robotic medical procedure, the method including: receiving a plurality of prior procedure data sets, wherein each prior procedure data set: (i) corresponds to an instance of the robotic medical procedure performed by using a robotic tool on a patient within a population, and (ii) defines one or more of a location or a movement of a patient, medical device, or robotic tool involved in the robotic medical procedure; a force applied by the robotic tool; or a timing of a step of the robotic medical procedure; receiving or identifying objective data defining one or more of a duration or a patient outcome of the robotic medical procedure; identifying a pattern across the plurality of prior procedure data sets, the pattern describing one or more of a location or a movement of a patient, medical device, or robotic tool involved in the robotic medical procedure, a force applied by the robotic tool, or a timing of a step of the robotic medical procedure that achieves the duration or the patient outcome defined by the objective data; receiving information about an instance of the robotic medical procedure to be performed in the future for a patient outside the population; automatically generating guidance for performing the robotic medical procedure, the guidance comprising a recommended location or movement of a patient, medical device, or robotic tool involved in the robotic medical procedure, force applied by the robotic tool, or timing of a step of the robotic medical procedure based on evaluating the pattern identified across the plurality of prior procedure data sets and the information received about the instance of the robotic medical procedure to be performed; and generating and presenting an electronic display of the guidance for performing the instance of the robotic medical procedure.

The storage medium may additionally or alternatively include one or more of the following features: the duration defined by the objective data may be a duration of a portion of the robotic medical procedure; each prior procedure data set may include information gathered by a robotic device associated with the robotic tool during the corresponding robotic medical procedure; identifying the pattern may include identifying an occurrence level of at least one of the location or the movement of the patient, medical device, or robotic tool across the plurality of prior procedure data sets; identifying the pattern across the plurality of prior procedure data sets may include describing a movement of the robotic tool during a portion of a procedure that achieves the duration defined by the objective data, wherein the duration is of the portion of the robotic medical procedure; the information about the instance of the robotic medical procedure to be performed may include information about at least one of: a patient, a type of procedure, an operating room characteristic, or a user's prior experience; and the medical device may be a table supporting the patient.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

The present disclosure is drawn to systems and methods for providing guidance for a robotic medical procedure. In one embodiment, a procedure optimizer may receive information corresponding to input procedures. The information may then be analyzed by the optimizer to determine patterns. The optimizer may further receive input related to a robotic medical procedure for which the optimizer will develop guidance. The optimizer may develop guidance, based on the pattern and the information related to the robotic medical procedure, to aid in the implementation of the robotic medical procedure.

EXEMPLARY EMBODIMENTS

Figure 1:
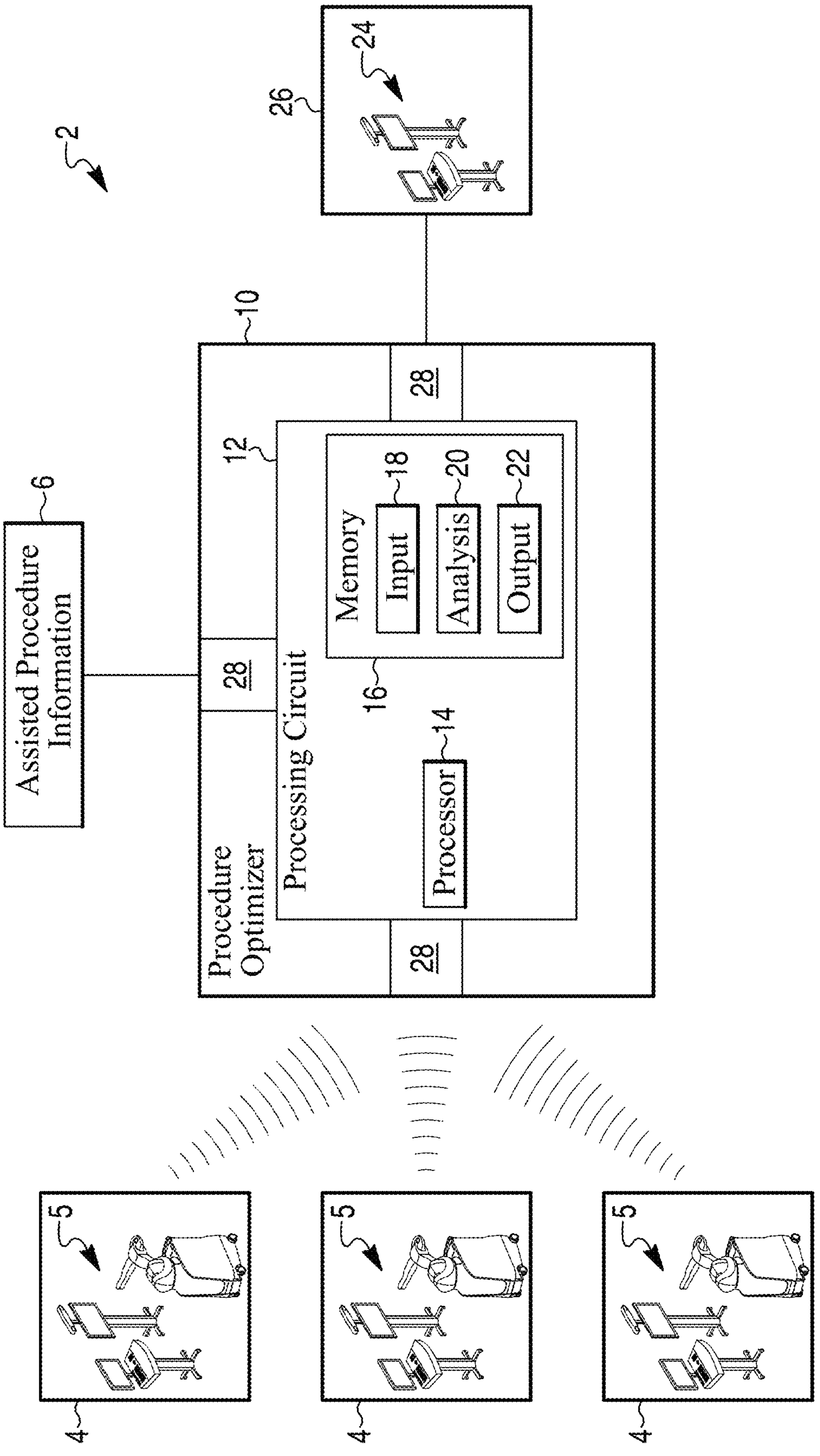
FIG. 1 illustrates a system for providing guidance for a robotic medical procedure, according to an exemplary embodiment.
Figure 2:
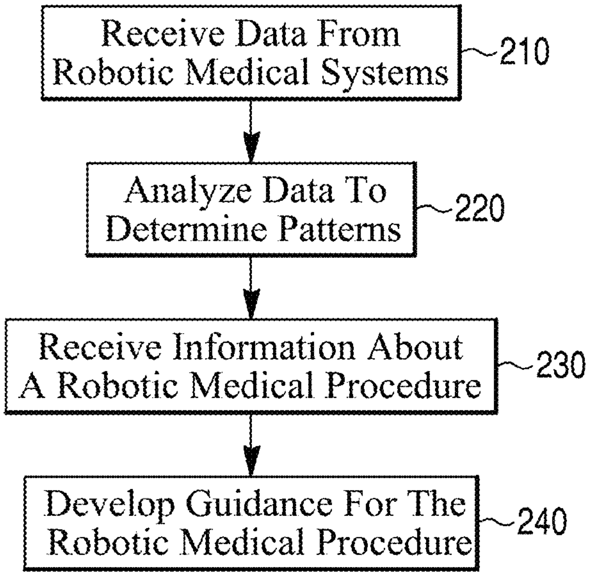
FIG. 2 illustrates a method for providing guidance for a robotic medical procedure, according to an exemplary embodiment.

FIG. 1 illustrates a system 2 for developing guidance for robotic medical procedures, and FIG. 2 illustrates a method for developing guidance. The system 2 includes a procedure optimizer 10. The procedure optimizer 10 may receive input procedure data 4 from multiple robotic systems 5 (FIG. 2, step 210). In one embodiment, each set of input procedure data 4 corresponds to a completed or in-progress robotic medical procedure performed by a user using a robotic system 5. In this disclosure, "user" is synonymous with "practitioner" and may be any person completing the described action (e.g., surgeon, technician, nurse, etc.). Among other components, each of the robotic systems 5 may include a robotic device, a guidance module, and a camera stand for tracking the patient and other objects. The guidance module and camera stand (referred to herein as guidance components 24) may include screens for providing output to a user. One or more of the robotic device, guidance module, or camera stand may store input procedure data 4 that may be retrieved by the procedure optimizer 10. Input procedure data 4 may alternatively be stored in any other component of the robotic system 5, or may be stored outside of the robotic system 5. The stored input procedure data 4 may be analyzed by the procedure optimizer 10 to determine patterns of characteristics of the corresponding medical procedures (FIG. 2, step 220).

The procedure optimizer 10 may further receive information about an assisted robotic medical procedure (referred to as assisted procedure information 6) (FIG. 1; FIG. 2, step 230). The procedure optimizer 10 may then develop guidance for the assisted procedure based on the analysis of input data 4 and the assisted procedure information 6 (FIG. 1; FIG. 2, step 240). In this disclosure, an "assisted procedure" refers to the robotic medical procedure for which guidance from the procedure optimizer 10 would be relevant. The term "assisted procedure" is used herein to distinguish the procedure the guidance is directed towards, or relevant to, from the procedures and their corresponding data 4 used as inputs to the procedure optimizer 10. The assisted procedure may or may not have been started or completed at the time the guidance is developed or provided to a user. Furthermore, the assisted procedure may be a planned procedure that never actually takes places, a procedure that is partially completed, or a procedure that has already been completed. The output provided by the procedure optimizer 10, which may be guidance relevant to the assisted procedure, may or may not actually be acted upon by a user, and if acted upon, the guidance may or may not in fact optimize the procedure with respect to a given metric.

Procedure Optimizer

The procedure optimizer 10 may be utilized to implement the various functions (e.g., calculations, processes, analyses) described herein. Procedure optimizer 10 may include a processing circuit 12 having a processor 14 and memory 16. Processor 14 can be implemented as a general purpose processor, an application specific integrated circuit (ASIC), one or more field programmable gate arrays (FPGAs), a group of processing components, or other suitable electronic processing components. Memory 16 (e.g., memory, memory unit, storage device, etc.) may be one or more devices (e.g., RAM, ROM, Flash-memory, hard disk storage, etc.) for storing data and/or computer code for completing or facilitating the various processes described in the present application. Memory 16 may be or include volatile memory or non-volatile memory. Memory 16 may include database components, object code components, script components, or any other type of information structure for supporting the various activities described in the present application. According to an exemplary embodiment, memory 16 may be communicably connected to processor 14 and may include computer code for executing one or more processes described herein. The memory 16 may contain a variety of modules, each capable of storing data and/or computer code related to specific types of functions. In one embodiment, memory 16 contains several modules related to medical procedures, such as an input module 18, an analysis module 20, and an output module 22.

It should be understood that the procedure optimizer 10 need not be contained in a single housing. Rather, components of procedure optimizer 10 may be located in various locations of the system 2 depicted in FIG. 1, or even in a remote location. Components of procedure optimizer 10, including components of the processor 14 and memory 16, may be located, for example, in components of different robotic systems 5 or in the robotic system components (e.g., in the guidance components 24) of the assisted procedure.

The present disclosure contemplates methods, systems, and program products on any machine-readable media for accomplishing various operations. The machine-readable media may be part of or may interface with the procedure optimizer 10. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Referring again to FIG. 1, the procedure optimizer 10 further includes one or more communication interfaces 28. The communication interfaces 28 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). For example, communication interfaces 28 can include an Ethernet card and port for sending and receiving data via an Ethernet-based communications link or network. In another example, communication interfaces 28 can include a Wi-Fi transceiver for communication via a wireless communications network. Thus, if the procedure optimizer 10 is physically separate from other components of the system 2 shown in FIG. 1, such as the robotic systems 5, an original location of the assisted procedure information 6, or the components of an assisted procedure, the communication interfaces 28 can enable wireless communications between the procedure optimizer 10 and these separate components.

Input Procedure Data

Figure 5:
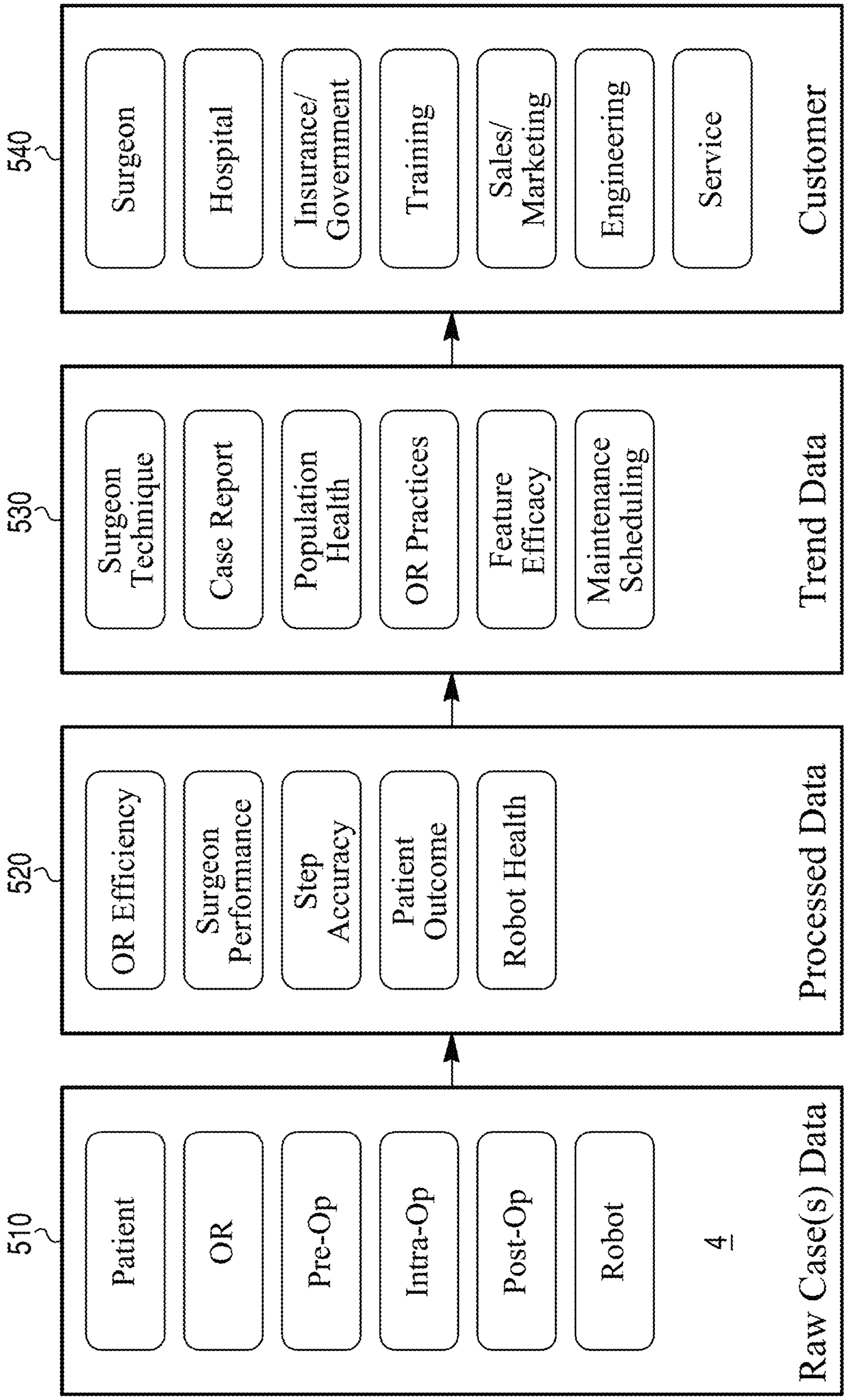
FIG. 5 illustrates a flow of input information from input procedures to a variety of customers, according to an exemplary embodiment.

Input procedure data 4 is data corresponding to a robotic medical procedure performed using a robotic system 5. The data 4 may relate to any characteristics of the corresponding input procedure. Referring to FIG. 5, the input procedure data 4 may include, for example, patient information (e.g., biometrics, patient images, comorbidities, allergies, etc.), operating room characteristics (e.g., size, setup), pre-operative information (e.g., a surgical plan, the type of procedure), intra-operative information (e.g., the performance of the procedure, how long certain steps of the procedure took), post-operative information (e.g., final positioning of any implants), and/or information related to any devices used during the procedure, such as a robot. The data 4 may have been input into the robotic system 5 prior to a procedure (e.g., manually by a user or by any form of data transfer) or may have been gathered, measured, recorded, or otherwise obtained by the robotic system 5 during the procedure. Robot data refers to any data 4 that was input into, measured, recorded, or otherwise gathered/obtained by a robotic device in association with a medical procedure that was performed using the robotic device. Data obtained during the procedure may be in the form of log files, although input procedure data 4 corresponding to a procedure may include log files in addition to other data corresponding to the procedure. In one embodiment, a set of input procedure data 4 corresponds to a single medical procedure performed using a robotic system 5.

Referring to FIG. 1 and step 210 of FIG. 2, the procedure optimizer 10 may receive any number of sets of input procedure data 4, with each set corresponding to a medical procedure. In one embodiment, the procedure optimizer 10 may receive sets of input procedure data 4 from several robotic systems 5, with numerous sets collected from each robotic system 5. Each set of input procedure data 4 collected from a single robotic system 5 may correspond to a different procedure performed using that robotic system 5. In other embodiments, the medical procedures corresponding to sets of input procedure data 4 received by the procedure optimizer 10 may have all been performed using the same robotic system 5, or each of the medical procedures may have been carried out using a different robotic system 5.

The input procedure data 4 received by the procedure optimizer 10 may include information indicative of characteristics of a corresponding input procedure. For example, the input procedure data 4 from a certain procedure might be indicative of a practitioner's technique for modifying bone or performing other portions of a procedure, how long a certain portion of the procedure took, the forces applied to a bone during a portion of the procedure, or where certain components of the robotic system or people were located during the procedure, among many other characteristics.

The input procedure data 4 may indicate a practitioner's technique for modifying bone, for example, by including log lines related to the position and orientation of a surgical tool over time. The robotic systems 5 may include tracking systems, which monitor the position and orientation of the patient and the robotic device, including a surgical tool, during the procedure. The data 4 related to the position and orientation of various components may be stored in a log file located in any component of the robotic system 5, such as in the robotic device, in a guidance module, or in the camera stand of the tracking system. The log files, with data 4 conveying the position and orientation of the tool during a procedure, may be received by the procedure optimizer 10 (e.g., by executing instructions contained in the input module 18 of memory 16), and may be analyzed by the procedure optimizer 10 (e.g., by executing instructions contained in the analysis module 20 of memory 16) to determine how a practitioner implemented a certain portion of the procedure.

In one example, the position and orientation data may indicate that the practitioner swept the tool from side-to-side to complete a certain portion of the procedure. A log file from a different procedure, however, may include data 4 indicating that the practitioner plunged the surgical tool into the bone several times, instead of sweeping the tool side-to-side, to complete the same portion of the procedure. Thus, each set of input procedure data 4 may be indicative of a characteristic of a corresponding procedure, such as the practitioner's technique during a certain portion of the procedure.

In a second example, the input procedure data 4 may include information indicative of how a practitioner completed a pre-operative range of motion test. In a knee surgery, for example, different practitioners may use different techniques to map the patient's range of motion. The input procedure data 4 may include log lines describing the position and orientation of the tibia and femur during the range of motion test of a corresponding procedure. The position and orientation data can be analyzed to determine how the practitioner manipulated the tibia and femur during the range of motion test. The data 4 from various procedures can be compared to determine how different practitioners completed similar range of motion tests, or to determine whether a single practitioner uses the same technique during different procedures.

In another example, the input procedure data 4 may include information indicative of the length of time of a certain portion of a procedure. Numerous tasks may be carried out during a procedure. In a knee replacement surgery, for example, tasks may include the pre-operative range of motion test described above; femur preparation, which may include using different tools to cut, sculpt, or otherwise modify the femur; tibia preparation, which may similarly include using different tools to cut, sculpt, or otherwise modify the bone; and implant placement. Analysis of the input procedure data 4 may indicate how long each portion and subportion of the procedure took. For example, the data 4 might indicate the total length of time for femur preparation or the length of time to complete a single bone cut.

In yet another example, the input procedure data 4 may be indicative of the forces applied to a bone during a portion of the corresponding procedure. In this embodiment, the robotic device may include a force sensor, and information related to the force sensor readings may be stored in the log file. The data 4 of the log file may then be analyzed to track force applied to the bone (e.g., by a surgical tool) during the procedure.

Tracking systems used during procedures may generate data 4, stored in a corresponding log file, related to placement of various components in the operating room. For example, data 4 may indicate the locations over time of the robotic device (including the surgical tool and base of the robotic device), the guidance module, the patient's anatomy (e.g., femur, tibia), and the tracking system camera, along with any other items tracked by the tracking system. The data 4 can be analyzed to determine the location of components during the procedure.

Data Analysis

Referring to step 220 of FIG. 2, the input procedure data 4 received from the robotic medical systems 5 (or other location) may be analyzed by the procedure optimizer 10 (e.g., by executing instructions stored in the analysis module 20). In one embodiment, the data 4 may be analyzed to determine a pattern of a characteristic across multiple input procedures. Analyzed characteristics may relate to practitioner technique, length of a portion of the procedure, forces applied to bone, location of objects or people during the procedure, or any other characteristic that may be recognized by analyzing data corresponding to a robotic medical procedure.

The analysis module 20 of procedure optimizer 10 may include instructions for analyzing the input procedure data 4, initially contained in log files or other forms, to determine a pattern of one or more characteristics across multiple procedures. In one embodiment, the analysis module 20 may process the log files using a standard extract, transform, and load procedure that transforms plain text files into database records. The analysis module 20 may further include statistical analysis processes to determine patterns in the input procedure data 4.

A pattern of a characteristic may be a description of the characteristic's general occurrence (or lack thereof), specific features of the characteristic, factors correlated with occurrence of the characteristic, or any other description of the characteristic. For example, in the example described above relating to side-to-side movement of a surgical tool, the pattern may be that the side-to-side technique is used in 75% of procedures (e.g., the side-to-side movement was seen in 75% of the analyzed log files). In another embodiment, the pattern may be a curve mapping the distance of a single sweep of a tool during the side-to-side movement portions of multiple procedures. Such a curve might provide information about the average distance of a sweep of the tool. In yet another embodiment, the pattern may be that 80% of the practitioners who use the side-to-side technique are left-handed.

In another embodiment, the characteristic of interest may be a technique for completing a range of motion test. The pattern of the characteristic recognized by the procedure optimizer 10 may be, for example, that 30% of practitioners use a first technique, 30% of practitioners use a second technique, and 40% of practitioners use a third technique. The pattern may additionally or alternatively identify specifics of the implementation of each technique (e.g., where the leg was positioned during a certain stage of the test across multiple procedures), or differences between the implementation of a certain technique among practitioners. The pattern may additionally or alternatively identify other information correlated with use of each of the techniques (e.g., if certain practitioners are more likely to use a certain technique).

If the characteristic relates to time, the pattern may be the average length of time of a certain portion of the procedure. In another embodiment, the pattern may be that using a certain technique for a task corresponds to a shorter completion time of the task. In yet another embodiment, the pattern may be that performing a set of tasks in a certain order results in a faster overall completion time. The pattern of the characteristic may be any description of the characteristic developed by analyzing multiple procedures.

A pattern related to the forces applied to the bone may be an average force applied during a certain portion of a procedure (e.g., the average force applied during a specific type of bone cut, with measurements taken during multiple procedures). In other examples, the pattern may be that practitioners with more experience use different force levels than practitioners with less experience; that a certain technique corresponds with use of a higher or lower amount of force; or that a certain practitioner uses different force levels depending on the setup of the operating room.

In yet another example, the pattern may relate to positioning of objects or people during a procedure. The pattern may be, for example, that a specific operating room layout or size typically results in placement of the robotic device, patient table, camera stand, patient, or user in a certain location. The pattern may additionally or alternatively be that certain types of procedures are typically completed with the robotic device in a certain location relative to the patient or other reference point, or that a certain practitioner typically positions objects a certain way in the operating room.

In sum, the procedure optimizer 10 may analyze the data 4 to identify a pattern of any characteristic of interest. The pattern may relate to the occurrence, specific features, implementation, correlated factors, or any other information descriptive of the characteristic that may be useful during development of guidance for an assisted procedure.

Assisted Procedure Information

Figure 3:
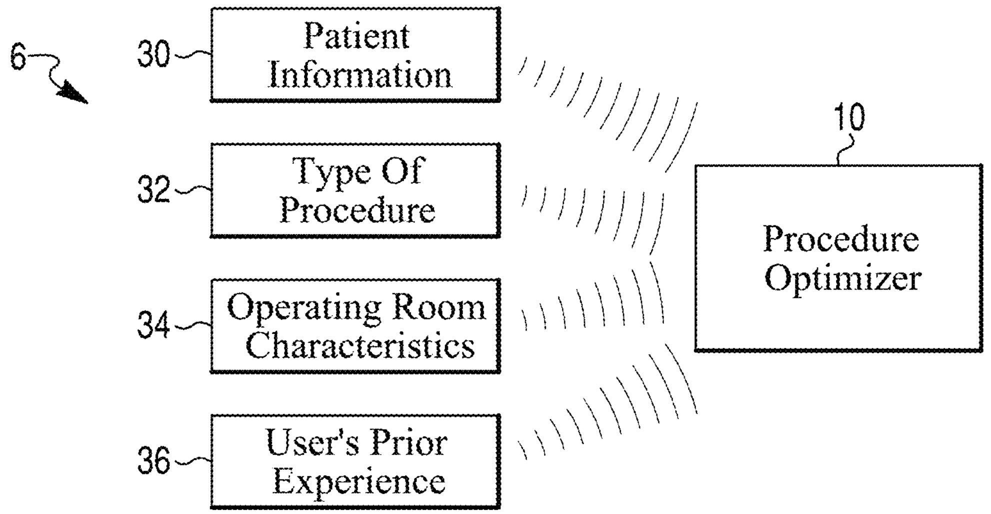
FIG. 3 illustrates input information related to an assisted robotic medical procedure, according to an exemplary embodiment.

Referring to FIG. 1 and step 230 of FIG. 2, the procedure optimizer 10 may receive assisted procedure information 6 about a procedure that the developed guidance will be directed towards. The assisted procedure information 6 may be any information about the assisted procedure, including information about the patient of the assisted procedure. FIG. 3 illustrates several examples of assisted procedure information 6, including patient information 30, type of procedure information 32, operating room characteristics 34, and user's prior experience information 36. Assisted procedure information 6 may be provided in any form, such as images (e.g., of the patient or operating room), data files, manual input by a user, or received from patient monitoring devices, and may be transmitted to the procedure optimizer 10 via a communication interface 28.

Patient information 30 may include various characteristics of the patient of the assisted procedure, such as height, weight, body mass index, bone density, bone structure, cartilage thickness, etc. The patient information 30 may be manually entered by a user, uploaded from a previously-existing image or text file, received from a patient monitoring device, or communicated in any other manner to the procedure optimizer 10 via communication interface 28. A patient monitoring device may be, for example, a device that monitors the patient's neural or cardiac activity.

Type of procedure information 32 may include the general type of assisted procedure (e.g., full or partial knee replacement; hip replacement; ankle, shoulder, or spine procedure; a procedure on a bone outside of a joint; or non-orthopedic procedures, such as on soft tissue). The information 32 may additionally or alternatively include a surgical plan with details of the assisted procedure, such as the planned shape and order of bone modifications or which tools (e.g., saw, burr) will be used during the procedure.

Operating room characteristics 34 may include the shape and size of the operating room and the planned placement of various people and objects during the procedure. For example, a surgical plan might indicate the initial placement of one or more of the patient table; the patient; the practitioner; other operating room personnel; the robotic device; the guidance module; the tracking system components; tools (e.g., retractors and other objects used during a procedure); or wires, tubing, and other equipment. During an assisted procedure, the system 5 may track any of these components, including portions of people (e.g., arms) or objects, using one or more tracking systems.

Finally, user's prior experience 36 may include information related to the user's previous experience performing robotic medical procedures. Information 36 might include general information about the number of procedures completed by the user (e.g., that the user has performed no robotic medical procedures, that the user has performed more than one, or that the user has performed numerous procedures), or may include detailed information about the specific procedures completed by the user. The procedure optimizer 10 may take the user's previous experience into account when developing guidance for the assisted procedure.

In one embodiment, the procedure optimizer 10 may receive further input in the form of rules. Rules may define outcomes and guidance that should result when the procedure optimizer 10 receives certain input. For example, one rule may define that for a patient weighing over 300 lbs, the procedure optimizer 10 should never recommend an implant size smaller than a certain threshold. Similarly, in another example, the rule may define that the procedure optimizer should not recommend an implant size above a certain threshold for a patient with a brittle femur bone. The rules may govern any aspect of a procedure or decision-making step.

Although the rules may be general rules applicable to many procedures, the rules may be considered a part of the assisted procedure information 6 because they may apply to the assisted procedure. Rules may be considered and applied by the procedure optimizer 10 when developing guidance. Similar to other assisted procedure information 6, rules may be manually entered by a user, uploaded from a previously-existing image or text file, or communicated in any other manner to the procedure optimizer 10, via a communication interface 28, and stored in the memory 16. Rules may be developed by a manual review of literature, by an analysis (manual or by the procedure optimizer 10) of the input procedure information 4, or by any other mechanism.

Guidance

Referring to FIG. 1 and step 240 of FIG. 2, the procedure optimizer 10 may develop output 26 by executing algorithms stored in the output module 22. In one embodiment, the output may be guidance for a practitioner to implement during the assisted procedure. Developing guidance may include generating revised robot instructions that, when executed, cause the robot to provide the guidance to a user. The guidance may be displayed on a screen of one or more guidance components 24. The guidance may be based on the pattern of the characteristic of input procedures recognized by the procedure optimizer 10 and on the assisted procedure information 6 received by the procedure optimizer 10.

Figure 4:
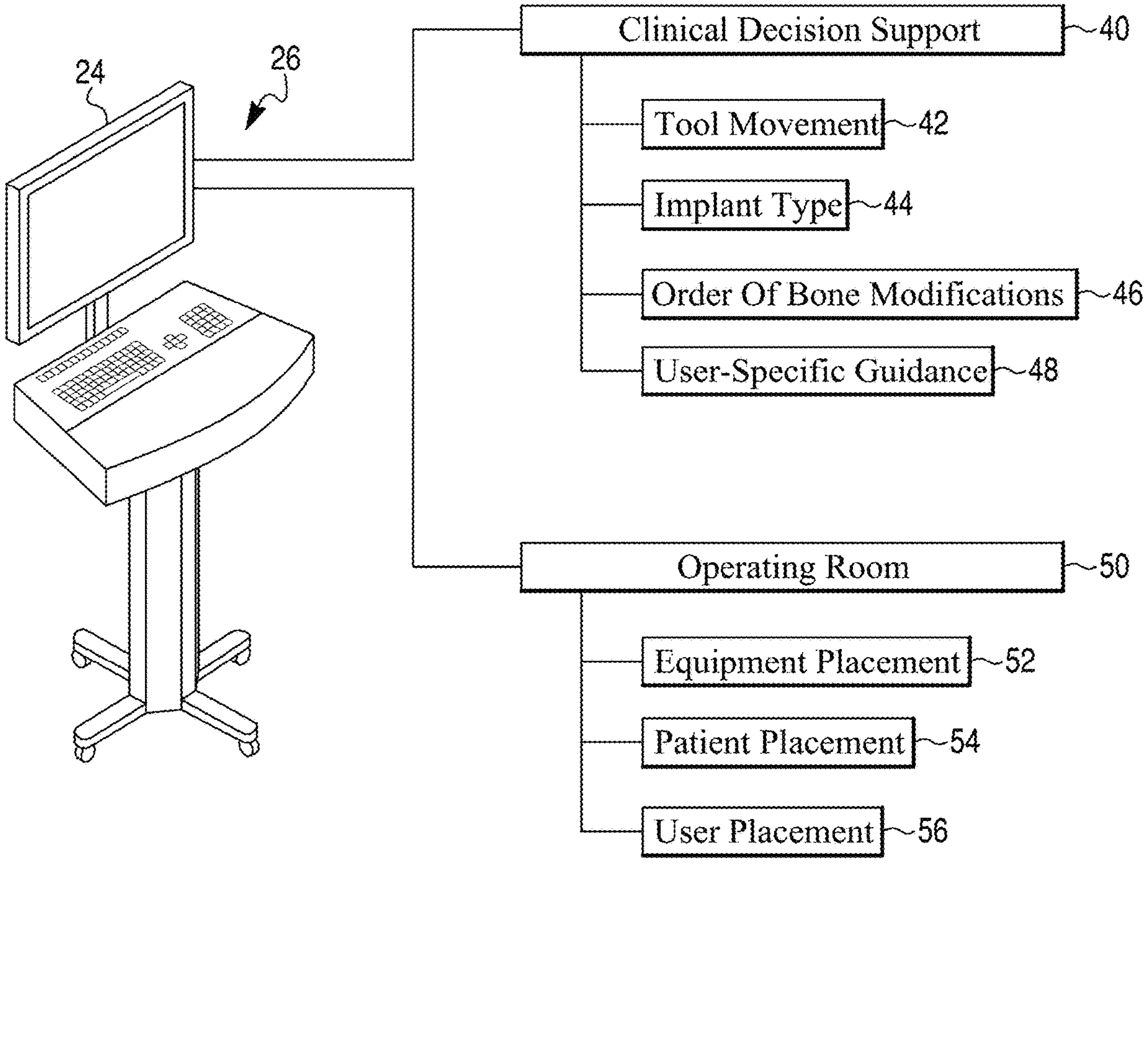
FIG. 4 illustrates output of a procedure optimizer, according to an exemplary embodiment.

FIG. 4 illustrates several exemplary types of guidance that may be developed by the procedure optimizer 10. The categories shown in FIG. 4 and the examples provided below are exemplary only. Certain types of guidance may fit into multiple categories or may fall into categories outside of those shown in FIG. 4. In one example, the guidance relates to clinical decision support 40. Clinical decision support 40 may include any type of guidance intended to help a practitioner make a decision before, during, or after a robotic surgical procedure.

In one embodiment, the guidance may help a practitioner make a decision related to tool movement 42. The guidance may be a recommendation to move the tool in a side-to-side motion to complete a certain portion of the procedure. This recommendation might be based on a recognition of a pattern, described above, that 75% of practitioners use the side-to-side motion. The guidance may alternatively be based on any other pattern recognized by the procedure optimizer. The guidance may be catered to the specific assisted procedure by also being based on the assisted procedure information 6. Thus, if a certain piece of information contained in the assisted procedure information 6 weighed strongly against a recommendation for a side-to-side motion (e.g., if the side-to-side motion is more difficult to implement and the user has no prior experience), the procedure optimizer 10 might take this into account and recommend a different technique. In this manner, the procedure optimizer 10 may synthesize data from the input procedures and information about the assisted procedure to develop targeted and appropriate guidance for the assisted procedure.

In another example, the procedure optimizer 10 may develop guidance related to implant type 44 (e.g., an implant or component of an implant to be used in a knee or hip replacement surgery) or implant positioning. The implant type 44 may be the size of the implant, the brand of the implant, the material of the implant, or any other features related to the implant. The recommendation related to the implant type 44 may be based on a recognized pattern of the types of implants used for patients of the input procedures. For example, the guidance may be based on the type of implant usually selected for patients with similar bone size and structure as the patient of the assisted procedure. In another example, the implant type 44 may be based on the implant type selected for other patients with a similar weight as the patient of the assisted procedure. Thus, the development of guidance related to the implant type 44 may be based on a pattern recognized in the data of the input procedures and information about the patient of the assisted procedure. Similarly, guidance related to implant positioning may be based on a recognized pattern of the positioning of implants in prior procedures with patients having similar characteristics (e.g., bone size, structure, weight) as the patient of the assisted procedure. In one embodiment, the procedure optimizer 10 may receive information about the long-term outcomes of patients of the input procedures as part of input procedure data 4. The procedure optimizer 10 may base its guidance for the assisted procedure at least in part on the implant type or positioning that led to the best long-term outcomes for the patients of the input procedures.

Although in some instances the pattern of the characteristics and the assisted procedure information may relate to the same type of information (e.g., bone structure of patients of the input procedures and bone structure of the patient of the assisted procedure), in other embodiments, the pattern and the assisted procedure information may relate to different types of information. For example, guidance related to implant type 44 may be based on a pattern that certain types of input procedures (e.g., unicondylar knee replacement surgeries) typically use a certain type of implant, and assisted procedure information about the bone structure of the patient.

In another example, the guidance may relate to the order of bone modifications 46. The procedure optimizer 10 may have recognized that practitioners of input procedures of a similar type as the assisted procedure usually performed the bone modifications in a certain order. Thus, the procedure optimizer 10 may develop guidance recommending that the practitioner of the assisted procedure perform the bone modifications in a similar order. However, if other factors weigh against performing the modifications in the same order as the input procedures, such as the assisted procedure patient's bone structure or even the operating room characteristics (e.g., initial placement of the robotic device), the procedure optimizer 10 might recommend a different order of bone modifications.

Another type of clinical decision support guidance may be user-specific guidance 48. User-specific guidance 48 may be any type of guidance that takes into account the experience, qualities, or other characteristics of the practitioner of the assisted procedure. The user-specific guidance 48 may take into account information such as, for example, how many robotic surgical procedures the practitioner has previously completed, the techniques the practitioner used to complete those surgical procedures, the handedness of the practitioner, or the preferences of the practitioner. This information about the practitioner may be included in the assisted procedure information 6 or may be included in the input procedure data 4 corresponding to procedures completed by the practitioner.

In one embodiment of user-specific guidance, the procedure optimizer 10 may output different sequences or numbers of guidance steps to practitioners having different levels of experience. For example, during a procedure being performed by a less experienced practitioner, the procedure optimizer 10 may provide a greater number of surgical steps, including more details, than would be provided to a practitioner having more experience. Thus, more experienced practitioners may receive more streamlined guidance during the procedure, commensurate with their experience. Over time, as a beginner practitioner becomes more experienced, the procedure optimizer 10 may reduce the number of details and/or steps that are shown to the practitioner during that practitioner's procedures. Similarly, in another embodiment, the procedure optimizer 10 may display certain messages to beginner practitioners that are not necessarily displayed to more experienced practitioners. For example, a relevant cautionary message (e.g., about a common but undesired action) may be displayed during a procedure for a beginning practitioner. As the practitioner becomes more experienced and does not perform the undesired action, the procedure optimizer 10 might discontinue displaying the message. On the other hand, if a particular experienced user might benefit from the message (e.g., because the user is performing a certain undesired action during a procedure or performed the undesired action during a past procedure), the procedure optimizer might display the message for that user.

Another category of guidance may include operating room guidance 50. This type of guidance may relate to placement of objects or people within the operating room. Equipment placement guidance 52 may be a recommendation to place the robotic device, guidance module, tracking system, patient table, or any other object in the operating room in a certain location. The recommendations may be based on the positioning of these items in input procedures with similar operating room characteristics (e.g., shape, size), and may take into account fixed objects or other constraints of the operating room being used for the assisted procedure. For example, some operating rooms may have a patient table that is fixed to the ground. Thus, the recommendation for the positioning of the remaining objects may be based on the positioning of the fixed patient table in addition to a pattern of the placement of the objects during the input procedures.

Guidance related to patient placement 54 may recommend that the user place the patient in a certain direction, or may be more specific and relate to certain specific positioning of the patient's leg or other portion of the anatomy. For example, if the patient was positioned facing a certain direction relative to the robotic device in prior procedures with similar operating room characteristics as the operating room characteristics 34 of the assisted procedure, the guidance may be a recommendation that the patient is positioned similarly relative to the robotic device to be used in the assisted procedure. Similarly, if the patient's leg was positioned with the knee at a certain angle at the start of a majority of the input procedures with similar characteristics as the assisted procedure, the guidance may be a recommendation to position the patient's knee at the certain angle at the start of the assisted procedure.

In another embodiment, the output guidance 26 may be a recommendation related to user placement 56. The user may be the person operating the robotic device, or may be any other person in the operating room (e.g., technicians, assistants, doctors, nurses, etc.). Guidance related to user placement 56 may be based on patterns of user placement recognized from the input procedure data 4 and on the assisted procedure information 6 (e.g., the type of procedure 32, operating room characteristics 34, etc.). The analysis of the input procedure data 4 may have revealed that certain types of procedure are completed faster when the user stands in a certain location relative to the patient and the robotic device. Thus, for an assisted procedure with similar characteristics, the guidance 26 may recommend that the user stand in a similar location relative to the patient and the robotic device to carry out the procedure.

Exemplary Workflow

FIG. 5 illustrates an exemplary workflow for providing guidance based on patterns in input procedure data 4. Step 510 of FIG. 5 includes input procedure data 4 that may be received by procedure optimizer 10. As described above, input procedure data 4 may include any information about a robotic medical procedure, such as patient information received in any manner, information about the operating room (OR) (e.g., OR size, OR setup), pre-operative information (e.g., procedures to carry out pre-operatively, such as the range of motion test described above), intra-operative information (e.g., tracking information, locations of the bone to contact for bone registration), post-operative information (e.g., a desired final implant location, information from rehabilitation), and/or information related to the surgical robot (e.g., joint angles, tolerances, whether the robot performed correctly during the procedure, movements of the robot) and other devices/equipment used during the procedure.

The processed data illustrated in step 520 may include information resulting from an analysis of the raw case data of step 510 and may be derivable from the raw case data shown in step 510. Processed data may include values that are comparable between more than one procedure and may aid in the determination of trend data in step 530. For example, processed data may include information relating to operating room efficiency (e.g., how quickly the OR staff completed the procedure). The information on efficiency may be derived from various types of raw case data, such as intra-operative data related to the time of each portion of the procedure and robot data related movements of the robot. Processed data may further include information on surgeon performance (e.g., how the surgeon holds certain tools). Surgeon performance information may be derived from pre-operative data, intra-operational data, and/or robot data, for example, by comparing a pre-operational plan with intra-operative tracking data and information on robot movements obtained during the procedure. Step accuracy (e.g., how accurately the surgeon/OR staff completed a step of the procedure) may similarly be derived from comparing pre-operative information with intra-operative information. Patient outcome information may include comparisons between pre-operative and post-operative data. Finally, information related to robot health (or the health of other instruments or devices used during a procedure), such as whether a part of the robot needs to be replaced, determining how much a motor has been used, or determining whether other instrumentation needs maintenance, may be derived from raw case data related to the robot or other devices.

By reviewing input procedure data 4 and processed data from multiple procedures, surgeons, operating rooms, hospitals, and/or regions, the procedure optimizer 10 may determine trend data in step 530. Trend data may include patterns that have been recognized by procedure optimizer 10. Examples of trend data include surgeon technique (e.g., that different techniques are used in different regions/hospitals, that different surgeons use different techniques), case reports (e.g., a synopsis of a number of different procedures that includes information about the procedures, such as, for example, bone registration accuracy, a comparison of the pre-operative plan to the post-operative outcome, etc.), population health (e.g., that patients in different regions/hospitals have better or different outcomes, that patients receiving a certain procedure have better or different outcomes), OR practices (e.g., that certain OR setups, staffing, or procedures result in better/different outcomes), feature efficacy (e.g., how well users implement steps of the procedure, how well a feature (e.g., a button) is working), and/or maintenance scheduling (e.g., if the trend data indicates that certain robotic devices or other devices need maintenance, either because outcomes of the procedures are changing or because the devices have undergone a certain number of procedures).

In step 540, the trend data obtained in step 530 may be applied in a variety of settings and provided to a number of customers to provide guidance to the customer. For example, to provide guidance to a surgeon, information about patients and operational data (e.g., pre-op, intra-op, and post-op) may be processed to determine surgeon performance (e.g., how well an implant was placed), step accuracy, (e.g., how well the surgeon performed during bone registration), and patient outcome. The surgeon may then receive a case report summarizing information about a variety of procedures. Based on the information in the case report, the procedure optimizer 10 may provide guidance to the surgeon to improve future procedures.

In another example, the procedure optimizer 10 may provide guidance to organizations, such as a hospital, an insurance company, or the government. The hospital may be interested in a variety of trend data, including data related to surgeon technique or maintenance scheduling, for example. In one example, a pattern related to maintenance scheduling may indicate that maintenance is being conducted too frequently, which may indicate that the hospital should investigate the equipment further.

Furthermore, the systems and methods described herein may be used by the hospital to optimize OR staffing and/or scheduling. In one example, the input procedure data 4 may include information related to the staff working during the corresponding medical procedure (e.g., names, case load, personality profiles, experience, etc.). In certain cases, the location of each staff member may be tracked during procedures using a navigation system. The trend data may include patterns related to the composition of the procedure staff and the clinical outcome of the patient. These trends may allow the procedure optimizer 10 to provide guidance assigning specific people to certain procedures. The procedure optimizer 10 further may receive information related to case schedules of one or more surgeons and/or operating rooms. The schedule may aid the procedure optimizer 10 in recommending certain personnel for certain procedures. For example, for a complicated case, the procedure optimizer 10 may recommend personnel who have experience in the procedure and have operated on patients with resulting good clinical outcomes, personnel who have not been too busy (e.g., overworked) in previous days, and/or personnel who are available during the scheduled or desired time slot (e.g., in the morning). In one example, the procedure optimizer 10 may recommend a first OR staff team to conduct robot setup and a second OR staff team to conduct a timeout procedure (e.g., a review of the patient, procedure, and other details prior to the surgical procedure).

In another example, the procedure optimizer 10 may be linked to a hospital's alert system to optimize OR utilization and scheduling. For example, if an OR staff member does not show up to a scheduled procedure, the procedure optimizer 10 may send an alert to the hospital's scheduling system. In another example, if a scheduled surgeon typically takes longer to perform a procedure, the procedure optimizer 10 may send an alert to the hospital's scheduling system to allow for adequate planning and scheduling of subsequent procedures. In yet another example, alerts may be sent if a surgeon is taking longer than scheduled during a procedure.

The robotic systems 5 may include tracking methods that may aid in inventory tracking and billing. In one example, the procedure optimizer 10 may receive information related to implants and other inventory to be used during a medical procedure (e.g., item number or type of implant, price, quantity available or quantity to be used during the procedure). In some prior art systems, personnel may track inventory, and bills based on manual tracking may be submitted by a device manufacturer to the hospital. In one example, robotic systems 5 may include an implant or other device/tool identifier, such as a barcode scanner or other visual or radiofrequency recognition system, to validate component usage (e.g., by scanning the packaging). This information then may be used to automatically generate and export an electronic surgical sheet to expedite the billing process. Furthermore, the sheets may provide a dynamic record of hospital inventory consumption. Tracking of inventory also may aid in accounting for disposable OR items, such as surgical sponges.

Referring again to FIG. 5, an insurance company may be interested in population health to aid in setting insurance rates. The government may be interested in population health for research or policy development, for example. Population health may be determined by analyzing patient data, pre-op information, and post-op information to determine patient outcomes for multiple patients.

The systems and methods for developing guidance described in this application may be used for training practitioners. Trend data may be provided to device manufacturers, surgeons, or any other personnel for training purposes. Trends related to surgeon technique and OR practices may be particularly helpful for training. For example, training related to surgeon technique may advise a surgeon not to hold a probe in a certain position. In another example, training may include suggestions to position an OR camera in a certain location.

The analysis of data from numerous prior procedures may illuminate general best practices (e.g., technique, equipment and user placement), which can be provided to a practitioner prior to or during a robotic procedure or during other training sessions. The best practices guidance may have been extracted by the procedure optimizer 10 during analysis of the input procedure information 4 or may have been received by the procedure optimizer 10 in the form of rules or other input. Providing practitioners with guidance on best practices may accelerate the learning process for practitioners using the robotic systems 5.

The systems and methods described herein may further be used to fine-tune a practitioner's technique by comparing input procedure data 4 from other practitioners to input procedure data 4 from the practitioner's own past procedures. For example, the procedure optimizer 10 might recognize that certain changes in the practitioner's technique would shorten the overall length of the procedure and may provide this guidance to the practitioner. In this example, the guidance provided to the trainee may be user-specific guidance 48, which is a form of clinical decision support, the "assisted procedure" may be a future procedure to be performed by the practitioner, and the assisted procedure information 6 may be information about the practitioner. In one embodiment, the guidance provided to the practitioner may be a recommendation to watch a training video. For example, the procedure optimizer 10 may recognize that the practitioner takes longer than other users to complete a certain phase of the procedure and may recommend a training video on technique to reduce completion time.

Trend data may further be provided to teams of a device manufacturer (e.g., of a device used in the medical procedures associated with input procedure data 4). For example, the sales/marketing teams of a manufacturer may be interested in trends related to population health and/or OR practices. Knowledge of these trends may aid sales/marketing teams in selling a medical device and/or advising hospital personnel how to use the medical device. The engineering team of a device manufacturer may be interested in surgeon technique and/or feature efficacy in order to aid in design improvements to the software and/or hardware of the device. Finally, the service team may be interested in the trend of maintenance scheduling to aid in efforts to reduce maintenance.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A tracking system comprising:

a plurality of robotic systems, wherein each of the plurality of robotic systems comprises a robotic device and a computer system;

a procedure optimizer in communication with the plurality of robotic systems across a network, wherein the procedure optimizer receives a plurality of prior procedure data sets, and each prior procedure data set includes first robot data associated with a prior robotic medical procedure;

wherein the procedure optimizer comprises an analysis module that statistically analyzes the plurality of prior procedure data sets to identify a pattern across the plurality of prior procedure data sets, the pattern including an occurrence level of a characteristic in the prior robotic medical procedures; and wherein the procedure optimizer (i) generates guidance based on comparing data associated with the pattern identified across the plurality of prior procedure data sets with second robot data received from one of the plurality of robotic systems during an instance of a robotic medical procedure, wherein the procedure optimizer assigns a first weight to the pattern based on an occurrence level of the characteristic, and a second weight to the second robot data based on inputs associated with the instance of the robotic medical procedure and (ii) generates and presents an electronic display of the guidance based on the first weight and the second weight.

2. The tracking system of claim 1, wherein the first robot data includes information gathered by a robotic device during a prior instance of a robotic medical procedure.

3. The tracking system of claim 2, wherein the electronic display of the guidance includes an input module allowing for user input.

4. The tracking system of claim 1, wherein the electronic display of the guidance is part of the computer system.

5. The tracking system of claim 1, wherein the procedure optimizer comprises a communication interface.

6. The tracking system of claim 5, wherein the procedure optimizer is physically separate from the plurality of robotic systems and wherein the communication interface transmits data between the procedure optimizer and the plurality of robotic systems.

7. The tracking system of claim 1, wherein the procedure optimizer is connected to an alert system of a hospital.

8. The tracking system of claim 1, wherein the computer system is at least partially integrated into the robotic device.

9. A system for generating and presenting an electronic display of guidance for performing a robotic medical procedure, comprising:

a plurality of robotic systems, each robotic system comprising:

a tracking system comprising a camera and one or more robotic tools; and one or more processors configured to execute the instructions to perform a method including:

receiving a plurality of prior procedure data sets, wherein each prior procedure data set: i) corresponds to an instance of the robotic medical procedure performed using the one or more robotic tools on a patient within a population, and ii) includes robot data associated with the robotic medical procedure, wherein the robot data is associated with a location and/or a movement of the one or more robotic tools;

identifying a pattern across the plurality of prior procedure data sets, the pattern describing a characteristic of the robotic medical procedure, wherein the characteristic is a location or a movement of the one or more robotic tools;

receiving information from the tracking system about an instance of the robotic medical procedure being performed for a patient outside the population, the information from the tracking system including a location or a movement of the one or more robotic tools in the instance of the robotic medical procedure;

automatically generating guidance based on comparing the characteristic identified by the pattern and the information received about the instance of the robotic medical procedure, the comparison including weighing the information from the tracking system about an instance of the robotic medical procedure against the pattern across the plurality of prior procedure data sets; and generating and presenting an electronic display of the guidance for the robotic medical procedure.

10. The system of claim 9, wherein the robot data is generated during the instance of the robotic medical procedure.

11. The system of claim 9, further comprising a computer system comprising a display interface.

12. The system of claim 11, wherein the electronic display of the guidance is displayed from the display interface.

13. The system of claim 9, wherein the robot data is associated with information indicative of a length of time of the robotic medical procedure.

14. The system of claim 9, wherein the robot data indicates an error in a location or a movement of the one or more robotic tools.

15. The system of claim 9, wherein the characteristic identified by the pattern includes a recommended location or movement of a robotic tool.

16. The system of claim 9, wherein the one or more processors communicates with an external source.

17. The system of claim 9, wherein identifying the pattern across the plurality of prior procedure data sets includes identifying the number of occurrences of a characteristic of the robot data.

18. A tracking system comprising:

a plurality of robotic systems, wherein each of the plurality of robotic systems comprises a robotic device and a computer system; and a remotely located procedure optimizer, in communication with the plurality of robotic systems across a network, wherein the procedure optimizer receives robot data obtained from each robotic device of the respective plurality of robotic systems;

wherein the procedure optimizer comprises an analysis module that statistically analyzes the robot data to identify a pattern across the plurality of robotic systems; and wherein the procedure optimizer (i) generates guidance based on comparing the pattern identified across the plurality of robotic systems and robot data received from a robotic device of the plurality of robotic systems during an instance of a robotic medical procedure, the comparing including weighing robot data received during an instance of the robotic medical procedure against the pattern identified across the plurality of robotic systems, and (ii) generates and presents an electronic display of the guidance.

19. The system of claim 18, wherein the electronic display of the guidance is part of the computer system and includes an input module allowing for user input.

* * * * *